United States Patent
Duerr et al.

(10) Patent No.: US 8,616,722 B2
(45) Date of Patent: Dec. 31, 2013

(54) INSPECTION LAMP WITH INTERCHANGEABLE MOUNT

(75) Inventors: John Duerr, Massapequa Park, NY (US); Gustavo Garcia, East Setauket, NY (US)

(73) Assignee: Spectronics Corporation, Westbury, NY (US)

( * ) Notice: Subject to any disclaimer, the term of this patent is extended or adjusted under 35 U.S.C. 154(b) by 549 days.

(21) Appl. No.: 12/862,100

(22) Filed: Aug. 24, 2010

(65) Prior Publication Data

US 2011/0050123 A1 Mar. 3, 2011

Related U.S. Application Data

(60) Provisional application No. 61/275,217, filed on Aug. 26, 2009.

(51) Int. Cl.
*F21L 4/00* (2006.01)
*H04M 1/22* (2006.01)

(52) U.S. Cl.
USPC ............ 362/191; 362/197; 362/269; 362/287

(58) Field of Classification Search
USPC ......... 362/105, 106, 103, 191, 194, 197, 269, 362/287, 297, 341, 345
See application file for complete search history.

(56) References Cited

U.S. PATENT DOCUMENTS

| | | | |
|---|---|---|---|
| 2005/0099824 A1* | 5/2005 | Dowling et al. | 362/572 |
| 2005/0237742 A1* | 10/2005 | Wang | 362/253 |
| 2007/0217188 A1* | 9/2007 | Klipstein et al. | 362/157 |
| 2008/0130267 A1* | 6/2008 | Dowling et al. | 362/96 |
| 2008/0173257 A1* | 7/2008 | Steiner et al. | 119/796 |
| 2008/0205038 A1* | 8/2008 | Becnel | 362/118 |
| 2008/0253109 A1* | 10/2008 | Canino et al. | 362/105 |
| 2009/0040751 A1* | 2/2009 | Coleman et al. | 362/191 |
| 2009/0225534 A1* | 9/2009 | Thomas et al. | 362/105 |
| 2010/0214766 A1* | 8/2010 | Hunt | 362/105 |

FOREIGN PATENT DOCUMENTS

CN 201047562 Y 4/2008

* cited by examiner

*Primary Examiner* — Anh Mai
*Assistant Examiner* — Kevin Quarterman
(74) *Attorney, Agent, or Firm* — Drinker Biddle & Reath LLP

(57) ABSTRACT

An inspection lamp with interchangeable mount including a housing having a front and rear, at least one blue/ultraviolet LED for emitting light in a blue/ultraviolet wavelength range from the front of the housing, at least one white LED for emitting broad spectrum visible light from the front of the housing, a mounting apparatus for removably mounting the housing to a mounting fixture, the mounting apparatus including a lamp adapter, and a slot located in the rear of the housing for slidably receiving the lamp adapter.

16 Claims, 7 Drawing Sheets

INSPECTION LAMP WITH INTERCHANGEABLE MOUNT

RELATED APPLICATION

This application is a regular application claiming priority to U.S. Provisional Application No. 61/275,217, filed Aug. 26, 2009, which is incorporated herein by reference in its entirety.

BACKGROUND

Leak detection and surface flaw non-destructive testing techniques often use fluorescent dye additives or fluorescent penetrants. These techniques rely upon the unique physical property of various materials to fluoresce when excited by certain wavelengths of light.

Fluorescence is generally understood to be a property that enables certain materials to absorb light energy and radiate visible light at a longer wavelength than the absorbed light. Without being limited to any specific theory, it is widely accepted that electrons in fluorescent materials are excited upon being illuminated by light energy of a specific wavelength, and light energy of a longer wavelength is radiated from these materials as the electrons return to the unexcited or ground state. The specific excitation and radiation wavelengths are characteristics of the particular fluorescent materials. The apparent brightness of a fluorescent material's luminescence is dependent, among other factors, on the wavelength emitted by the material and the intensity of the incident radiation that excites the material.

Lamps emitting radiation that excites fluorescence have been used for a wide variety of purposes, including, but not limited to, forensic inspection, readmission control, counterfeit currency detection, contamination inspection, non-destructive testing, and detecting leaks in air conditioning and other fluid-containing systems. The lamplight is commonly in the ultraviolet (UV) or in the visible blue-violet range, exciting a fluorescence somewhere in the visible range. The fluorescent material may be deliberately provided. For example, some banknotes have a fluorescent marker embedded in the paper and the UV light is used to detect the otherwise hidden marker. In another example, one method for detecting leaks in an air conditioning system is through the use of fluorescent dyes that are added to and mixed with the refrigerant in the system, with the combination of refrigerant and dye circulating through the air conditioning system. This method was first pioneered by Spectronics Corporation, the assignee of the present invention. In these leak detection systems, the dye circulates through the system, eventually seeping out at the source of the leak. When exposed to a suitable light source, such as an ultraviolet (UV) light, the dye fluoresces, thus highlighting the source of the leak. Stamps using an ink that is visible only by fluorescence under an ultraviolet lamp are used as re-admission stamps at entertainment events.

The fluorescence may be an incidental property of some material that it is desired to detect, measure, or observe. For example, many biological materials, including rodent hair and urine, are naturally fluorescent. Other examples of the use of fluorescence include the detection of counterfeit currency and other documents. Many minerals can be recognized or distinguished by their levels and colors of natural fluorescence.

Ultraviolet lamps may also be used to produce an effect on an object, for example, in sterilization, erasing EPROMs, or DNA/RNA cross-linking or otherwise setting or hardening various plastic materials. The visibility of the fluorescent response is increased when the intensity of other visible light is reduced, so that the fluorescent response is not masked or washed-out by other light. Thus, ultraviolet lamps directed in otherwise dark conditions at a system containing a UV responsive fluorescent material may reveal the fluorescent material glowing against the dark background.

Many current fluorescence-exciting lamps emit light in long wave ultraviolet (UV-A) wavelength range of about 320 nm to about 400 nm, for example, around 365 nm, or in the medium wave ultraviolet (UV-B) range from about 280 nm to about 320 nm, for example, around 315 nm, or in the short wave ultraviolet (UV-C) range, for example, around 254 nm, or in the visible violet/blue range from about 400 nm to about 480 nm within the electromagnetic spectrum.

SUMMARY

An embodiment of an inspection lamp with interchangeable mount is disclosed, the lamp including a housing having a front and rear, at least one blue/ultraviolet LED for emitting light in a blue/ultraviolet wavelength range from the front of the housing, and at least one white (visible) LED for emitting broad spectrum visible light from the front of the housing. The lamp further includes a mounting apparatus for removably mounting the housing to a mounting fixture, the mounting apparatus including a lamp adapter. A slot is located in the rear of the housing for slidably receiving the lamp adapter.

Another embodiment of an inspection lamp with interchangeable mount is disclosed, the lamp including a housing having a front and a rear, the rear of the housing including a mounting slot. In the housing are two blue/ultraviolet LEDs for emitting light in the blue/ultraviolet wavelength range from the front of the housing and three white (visible) LEDs for emitting broad spectrum visible light from the front of the housing. The lamp further includes a mounting apparatus for removably mounting the housing to a mounting fixture, the mounting apparatus including a lamp mounting tab adapted to be removably received into the mounting slot on the rear of the housing and a spring-loaded latch securing mechanism, the mounting apparatus further including a fixture adapter hingedly mounted to the lamp mounting tab such that when the fixture adapter is mounted to a mounting fixture the inspection lamp can pivot upward and downward with respect to the mounting fixture. The lamp also includes a splash shield removably mounted to the front of the housing for protecting the LEDs, the splash shield being at least partially transparent to ultraviolet and white light.

DETAILED DESCRIPTION

Figure 1:
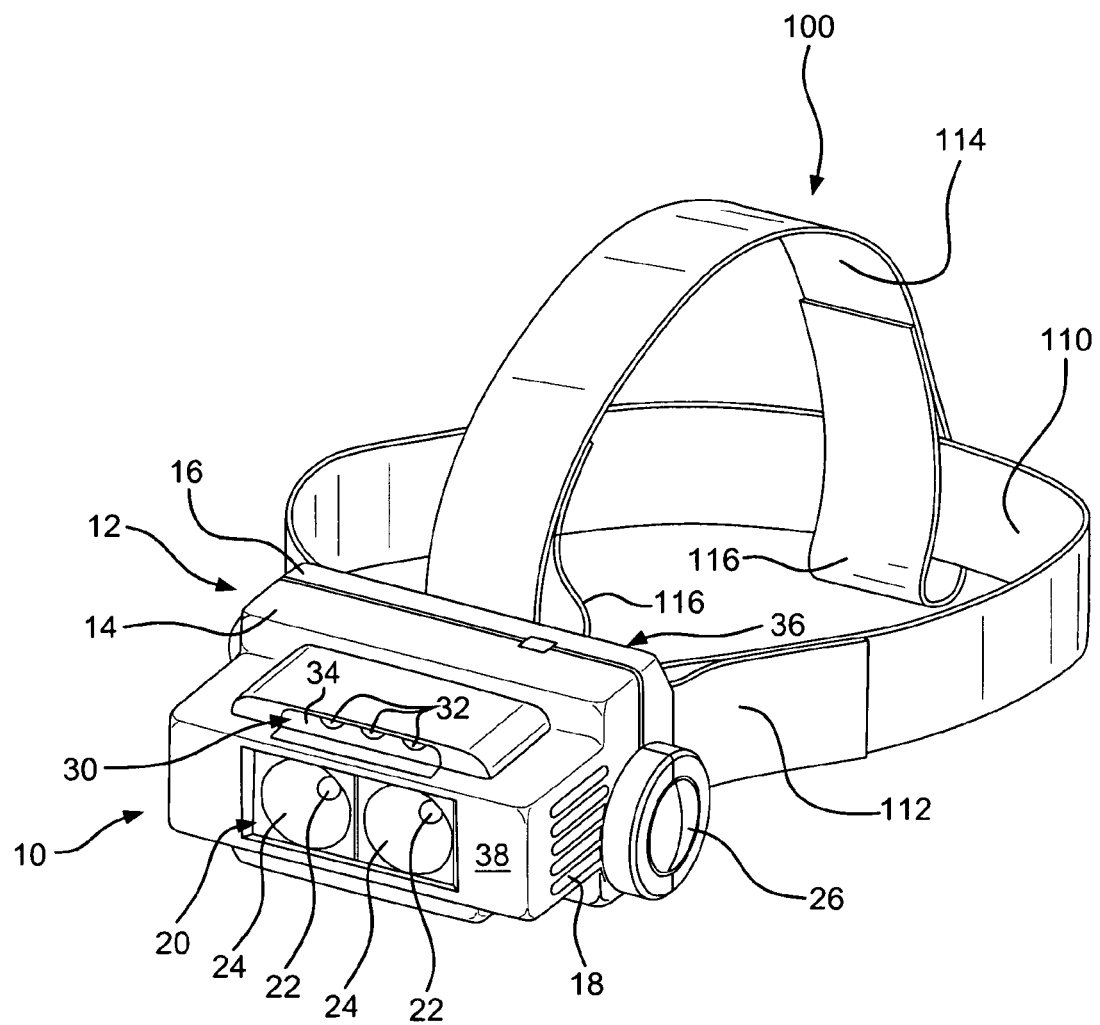
FIG. 1 is a perspective view showing an inspection lamp mounted to a head mounting fixture.

An inspection lamp 10 is depicted in FIG. 1 mounted to a head mounting fixture 100. As shown, the inspection lamp 10 has a two-part housing 12 including a front housing cover 14 and a rear housing cover 16. The housing covers 14 and 16 can be snapped, clipped, of otherwise fastened together by conventional means. The housing 12 encloses and protects internal components of the lamp 10. An externally accessible switch 26 enables the lamp 10 to be turned on and off and/or to be operated in different modes, as described in detail below. Vent slots 18 with or without an internal cooling fan (not shown) may be included in the housing 12 to provide for ventilation to cool the lamp 10 and its internal electrical components. The lamp 10 has a front 38 and a rear 36. Light is directed outwardly from the front 38 of the lamp 10. As will be discussed below, the lamp 10 can be interchangeably mounted to any of a number of fixtures by attaching the rear 36 of the lamp 10 to a mount depending on the desired use of the light emitted by the lamp 10.

Mounted in a recessed position in the front housing member 14 of the inspection lamp 10 is an ultraviolet (UV) or blue LED array 20 which includes one or more ultraviolet (or blue) LEDs 22 for emitting ultraviolet/blue light (e.g., light having a wavelength less than or equal to approximatley 500 nm). Each LED 22 (or all the LEDs 22) is surrounded by a chamber 24. In one embodiment, the chamber 24 includes a lens for focusing or dispersing the emitted light from the LEDs 22 toward a target object to be illuminated. In another embodiment, the chamber 24 includes a reflector for directing the light emitted by the LEDs 22 in a frontward direction toward the target object, and may also focus or disperse the light. In another embodiment, the chamber 24 includes a lens and a reflector. As shown, the UV LED array 20 includes two UV LEDs 22, although it is understood that one LED 22 or three or more LEDs 22 could be used.

Also mounted in a recessed position in the front housing member 12 of the inspection lamp 10 is a white or visible LED array 30 which includes one or more white or other visible LEDs 32 for emitting broad spectrum visible light that is preferably white. Each LED (or all the LEDs) 32 is surrounded by a chamber 34. In one embodiment, the chamber 34 includes a lens for focusing or dispersing the emitted light from the LEDs 32 toward a target object to be illuminated. In another embodiment, the chamber 34 includes a reflector for directing the light emitted by the LEDs 32 in a frontward direction toward the target object, and may also focus or disperse the light. In another embodiment, the chamber 34 includes a lens and a reflector. As shown, the preferred white LED array 30 includes three white LEDs 32, although it is understood that one, two, or four or more white LEDs 32 could be used. The lamp 10 can further include fans or heat sinks operating in conjunction with the vent slots 18 to manage the heat load generated by the LEDs 22 and 32.

Figure 2:
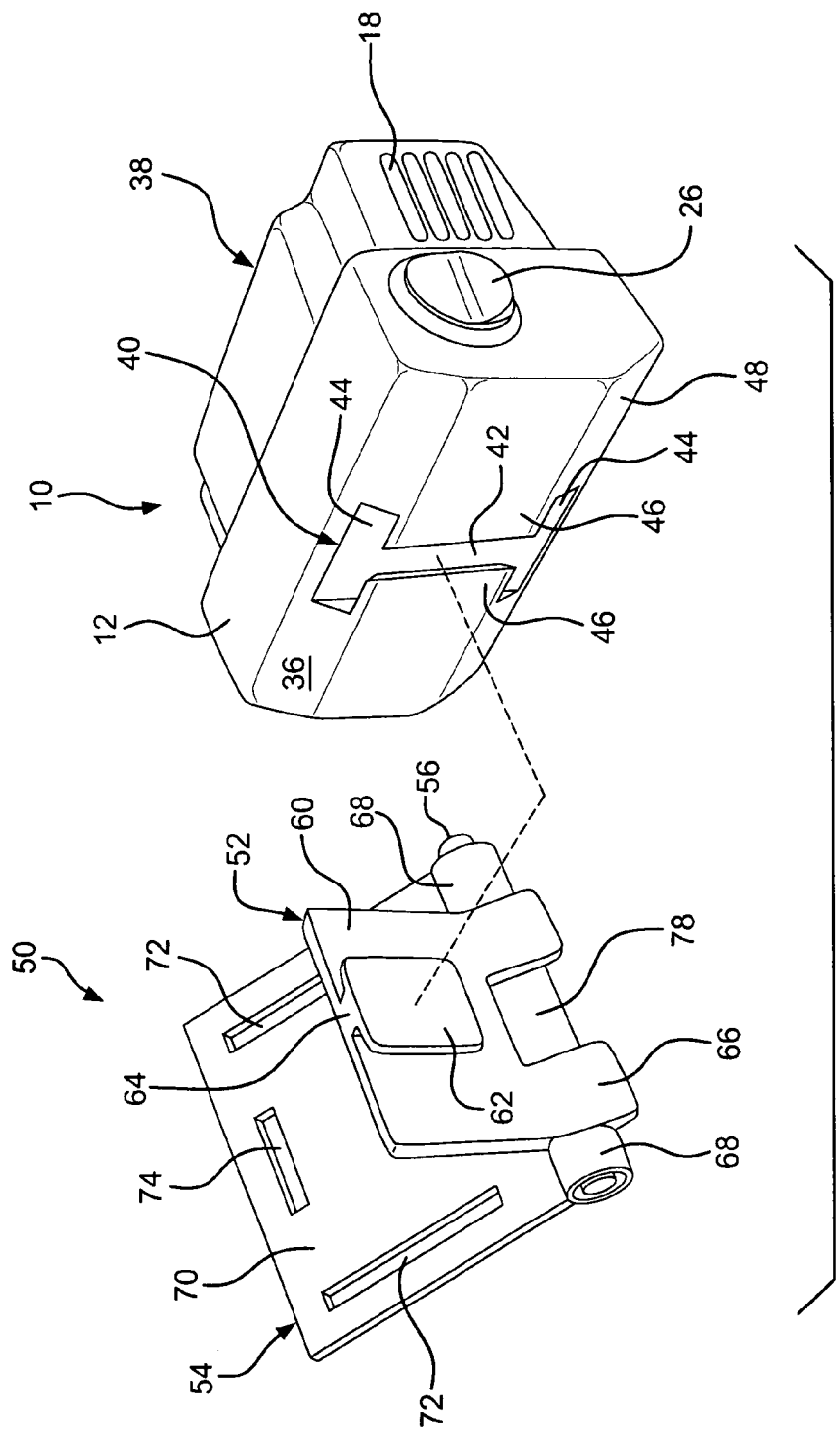
FIG. 2 is an exploded perspective view showing an inspection lamp and a mounting apparatus.

FIG. 2 depicts a rear view of the inspection lamp 10 detached from a mounting apparatus or support 50. The mounting apparatus 50 includes lamp adapter 52 and a fixture adapter 54. The lamp adapter 52 may be attached to the fixture adapter 54 through a pivotable connection including a pin 56 such that when the fixture adapter 54 is held fixed with respect to a mounting fixture, the lamp adapter 52 can pivot about the pin 56. Such a pivotable connection enables the direction of light emitted by the LEDs 22 and 32 to be adjusted between a generally upward-angled and downward-angled direction with respect fixture adapter 54, which will be fixed to a mounting fixture.

The lamp adapter 52 includes a support plate 60, a mounting tab 62, and an interconnecting member or rib 64 supporting the mounting tab 62 in a spaced apart relationship to the support plate 60. A lower portion 66 of the mounting plate 60 is preferably angled slightly frontwardly to prevent the lamp 10 from disengaging from the lamp adapter 52. A hinge knuckle 68 preferably extends laterally from a lower portion 66 of the mounting plate 62 and receives the pin 56 to enable the lamp adapter 52 to pivot about the pin 56.

The rear 36 of the lamp housing 12 includes a recessed slot 40 for receiving the mounting tab 62 of the lamp adapter 52. The slot 40 is formed by a generally vertical opening 42 located between a pair of lateral tabs 46. A generally horizontal opening 44 is formed at least at the lower end, and preferably also at the upper end of the vertical opening 42 to provide access for engagement and disengagement of the mounting tab 62 into the slot 40. In particular, the upper end of the mounting tab 62 is inserted into the lower horizontal opening 44 such that the interconnecting member 64 is aligned with the vertical opening 42. The depth of the interconnecting member 64 is approximately equal to the thickness of each of the lateral tabs 46 to ensure a snug fit between the lamp adapter 52 and the housing 12 as the mounting tab 62 is captured in the slot 40. The housing 12 slides downward onto the lamp adapter 52 so that the mounting tab 62 is received into the recessed slot 40 behind the lateral tabs 46, until the angled lower portion 66 or other stop contacts a contact surface 48 on the rear 36 of the housing, thus preventing the housing 12 from sliding further downward and off of the lamp adapter 52. The lamp 10 can be removed from the lamp adapter 52 by simply raising the lamp 10 vertically relative to the lamp adapter 52 to slide the mounting tab 62 and interconnecting member 64 out of the recessed slot 40.

The mounting fixture adapter 54 includes a support plate 70, preferably one or more fastening slots 72 and 74, and a hinge knuckle 78 extending from the support plate 70 for receiving the pin 56 to enable the mounting fixture adapter 54 to pivot about the pin 56.

Figure 7:
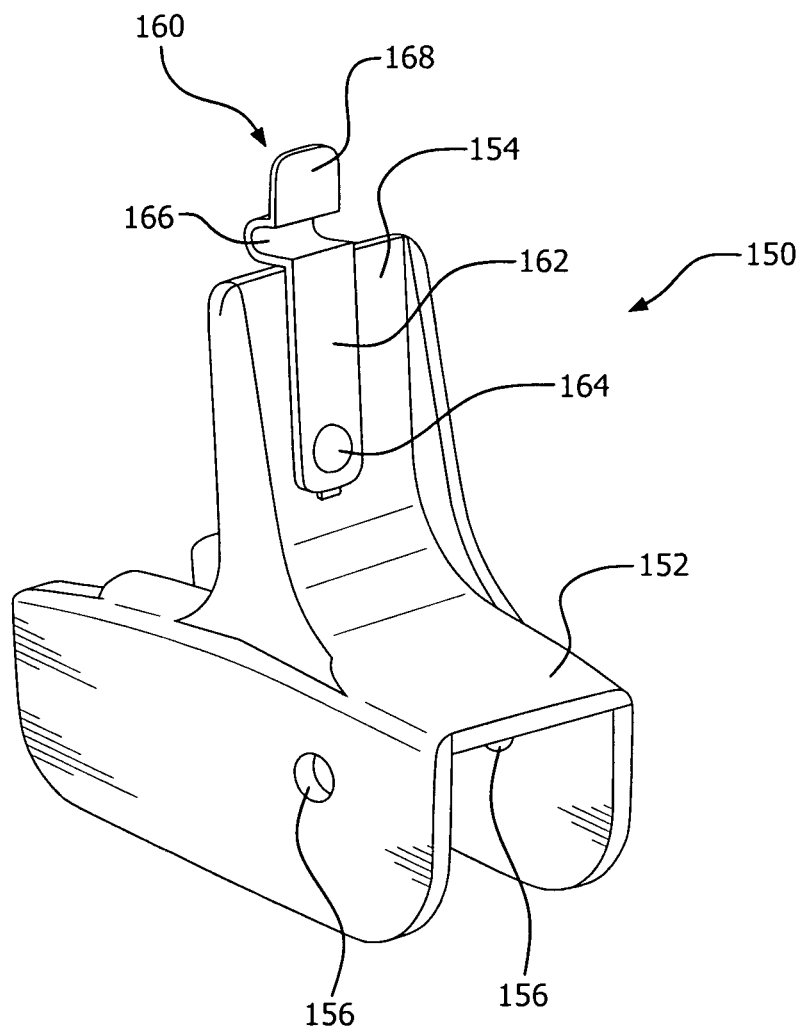
FIG. 7 is a perspective view showing an alternative mounting apparatus for an inspection lamp.

An alternative mounting apparatus 150 is shown in FIG. 7. The mounting apparatus 150 includes a base member 152 and a lamp adapter 154 extending outwardly therefrom. A mounting slot on the inspection lamp 10, such as the slot 40, slides onto the lamp adapter 154. The mounting apparatus 150 is pivotably affixed to a support structure such as a head mounting fixture or a spray can mounting fixture (discussed below) via a pair of pin mounting holes 156 combined with a mounting pin (not shown). The mounting apparatus 150 has a securing mechanism 160 that includes a spring member 162 fastened at one end to the lamp adapter 154 by a fastener 164 such as a rivet. The spring member 162 includes a latching protrusion 166 that is wider than the slot 40 and a finger tab 168 for actuating the spring member 162.

When the inspection lamp 10 is being installed onto the lamp adapter 154, the spring member 162 flexes away from the lamp adapter 154 to allow the latching protrusion 166 to pass over rear 36 of the housing 12. When the slot 40 of the inspection lamp 10 is fully engaged with the lamp adapter 154, the latching protrusion 166 springs into place above the slot 40 to prevent the lamp 10 from sliding off of the lamp adapter 154. To remove the lamp 10 from the lamp adapter 154, the spring member 162 is flexed by applying force to the finger tab 168 while sliding the lamp 10 with respect to the lamp adapter 154 to allow the latching protrusion 166 to pass over the rear 36 of the housing 12.

As shown in FIG. 1, the lamp 10 may be mounted to a head mounting fixture 100. The head mounting fixture 100 has a circumferential head strap 110 for fitting around the perimeter of a user's head and an overhead strap 114 for fitting across the top of a user's head. The straps 110 and 114 can be made from fabric, elastic, plastic, or other material known in the art, preferably one sufficiently flexible to accommodate the shape of a user's head. The circumferential strap 110 is connected to the mounting fixture adapter 54 by looped ends 112 of the strap 110 being received into the slots 72 on either side of the support plate 70. The overhead strap 114 is affixed to the circumferential strap 110 at a rear end by one loop 116 and to the slot 74 in the support plate 70 at a front end by another loop 116. The loops 112 and 116 can be secured by hook and loop type fasteners, stitching, snaps, buckles, or other conventional adjustable attachment means. Other mechanisms can be used for attaching the mounting fixture adapter 54 to the head mounting fixture 100, including hook and loop fasters, snaps, clips, adhesive, etc. In one embodiment, instead of a head mounting fixture 100, the mounting apparatus 50 can be mounted to a helmet or a hardhat.

When the head mounting fixture 100 is worn by a user and the lamp 10 is mounted to the head mounting fixture 100 via the mounting apparatus 50, the lamp may be pivoted upward and downward to various angles as desired, to project the light emitted by the LEDs 22 and 32 toward a target object to be illuminated.

Figure 3:
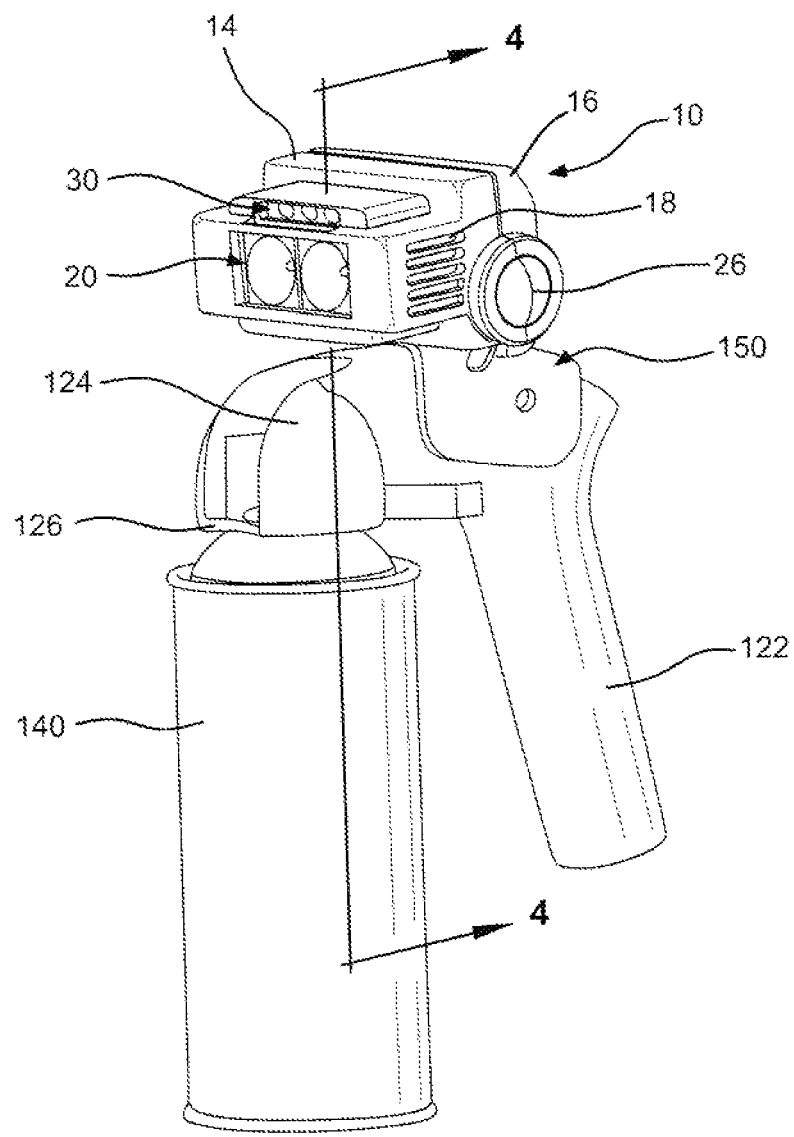
FIG. 3 is a perspective view showing an inspection lamp mounted to a spray can via a spray can mounting fixture.

The recessed slot 40 in the housing 12 is adapted to receive any number of various mounting apparatuses each designed for one or more specific use or uses. For example, as shown in FIG. 3, the lamp 10 can be mounted to a spray can 140 using a spray can mounting fixture 120. The spray can mounting fixture 120 includes a spray can nozzle shroud 124 and a handle 122 extending rearwardly from the nozzle shroud 124. The fixture 120 attaches to the rolled rim 120 of the spray can 140 immediately beneath the spray nozzle 144 by an attachment mechanism 126. The attachment mechanism 126 is sufficiently flexible to readily snap over the rolled rim 142 of the spray can 140. For example, the nozzle shroud 124 and attachment mechanism 126 can be made from plastic that can deform sufficiently to slip over the rolled rim 142 and then return to its original size and shape to retain the rolled rim 142 within the nozzle shroud 124. Other known attachment mechanisms can be similarly employed.

Figure 4:
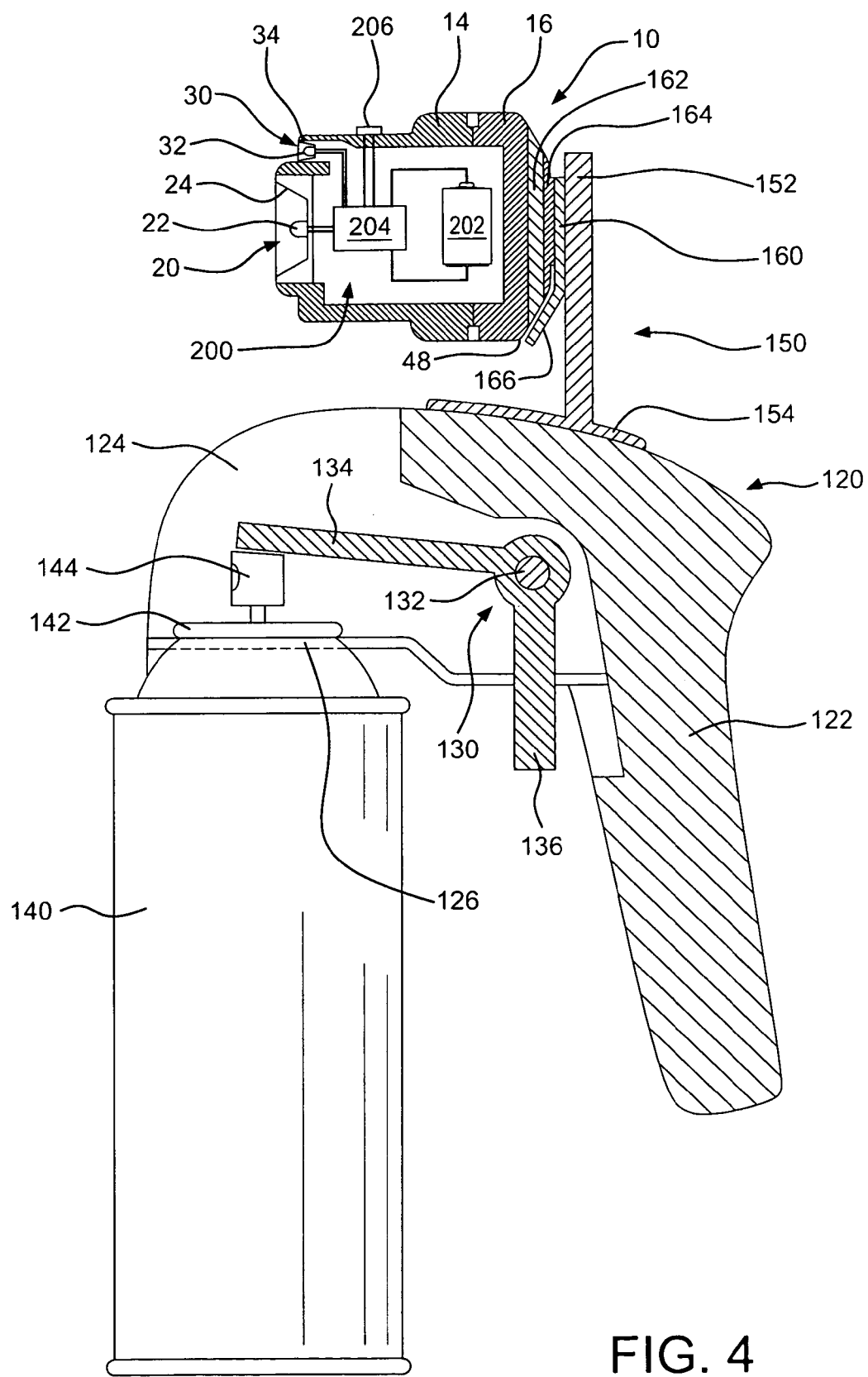
FIG. 4 is a cross-sectional view of the inspection lamp and spray can mounting fixture mounted to a spray can of FIG. 3.
Figure 5A:
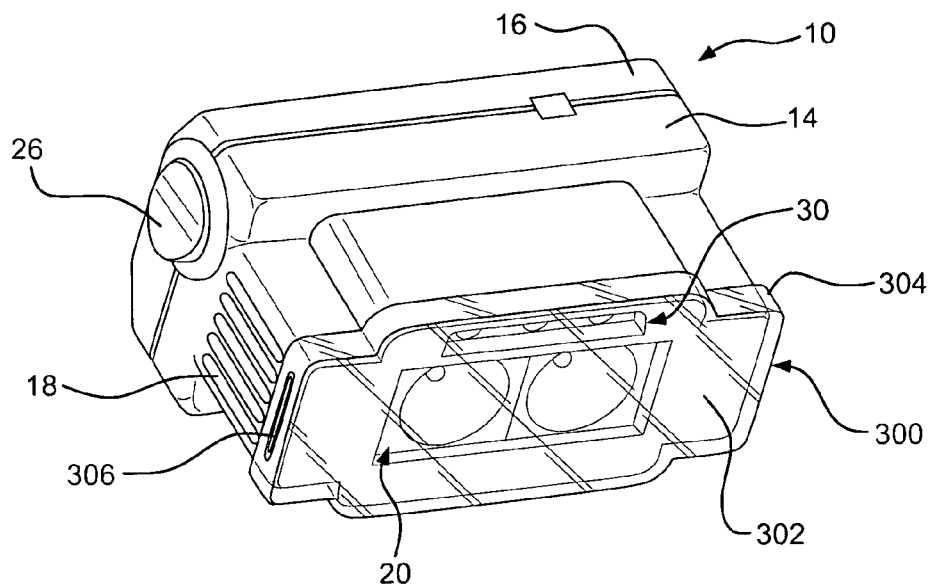
FIGS. 5A and 5B are perspective views showing an inspection lamp including a splash shield installed and removed from the lamp, respectively.
Figure 5B:
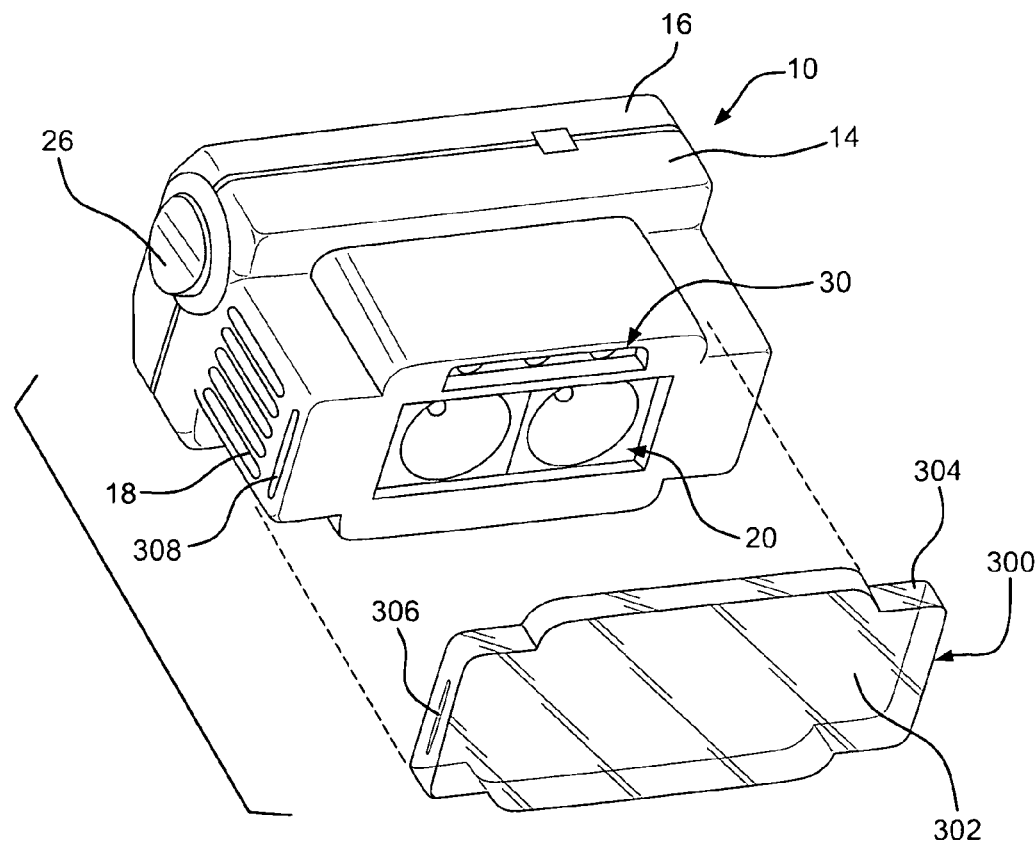

As depicted in FIG. 4, a mounting apparatus 150 interconnects the spray can mounting fixture 120 to the lamp housing 12. The mounting apparatus 150 includes a vertical member 152 supporting a mounting plate 160 and horizontal member 154 that forms a base for the vertical member 152 by which the mounting apparatus 150 is affixed to the handle 122 of the spray can mounting fixture 120. A mounting tab 162 is supported from the mounting plate 160 by an interconnecting member 164. A lower portion 166 of the mounting plate 160 is angled slightly forward to mate with the surface 48 of the housing 12 to prevent the lamp 10 from disengaging from the mounting tab 162.

The spray can mounting fixture 120 includes an actuator 130 for actuating the spray nozzle 144. The actuator 130 is pivotably mounted by a pin 132 to pivot with respect to the handle 122, and thus with respect to the nozzle 144. The actuator includes a finger trigger 136 disposed in one direction from the pin 132 and a nozzle trigger 134 disposed in another direction from the pin 132, such that when a user pulls the finger trigger 136 rearwardly toward the handle 122, the nozzle trigger 134 pivots downwardly to apply force to the nozzle 144, thus triggering the nozzle 144 to spray contents of the spray can 140 in a frontward direction.

As shown in FIG. 4, the lamp 10 includes internal circuitry 200 for providing power and control to the LEDs 22 and 32. In particular, the circuitry 200 includes a controller 204 and a power source 202. The power source 202 provides power to operate the controller 204 and to illuminate the LEDs 22 and 32, as well as to illuminate a power-on indicator light 206. The controller 204 can operate the lamp 10 in multiple operating modes, including but not limited to a mode in which only one or more of the UV LEDs 22 is energized, a mode in which only one or more of the white LEDs 32 is energized, and a mode in which both one or more of the UV LEDs 22 and one or more of the white LEDs 32 are energized.

The lamp 10 can further include a removeable ultraviolet-transmitting splash shield 300. The splash shield 300 is at least partially transparent to ultraviolet light and to visible white (broad spectrum visible) light. The splash shield protects the LED arrays 20 and 30 from splashing fluorescing fluid or other substances that may be present in the target area, while transmitting UV light emitted by the UV LEDs 22 and broad spectrum visible light emitted by the visible (white light) LEDs 32. The shield 300 includes a lens 302 and a rim 304 for fastening the shield 300 to the housing 12. The shield 300 can include a tab 306 to aid in retaining the shield 300 on the lamp 10, the tab 306 being received into a mating detent 308 in the housing 12. The shield 300 is made from a material that is at least partially transparent to UV and visible light, such as acrylite H12-003 sold by Cyro Industries. In one embodiment, the shield 300 is disposable. It is also contemplated that instead of a clip-on splash shield as shown, the shield may be a disposable cover sheet that includes adhesive along a peripheral edge for removably attaching to the front of the housing.

Figure 6:
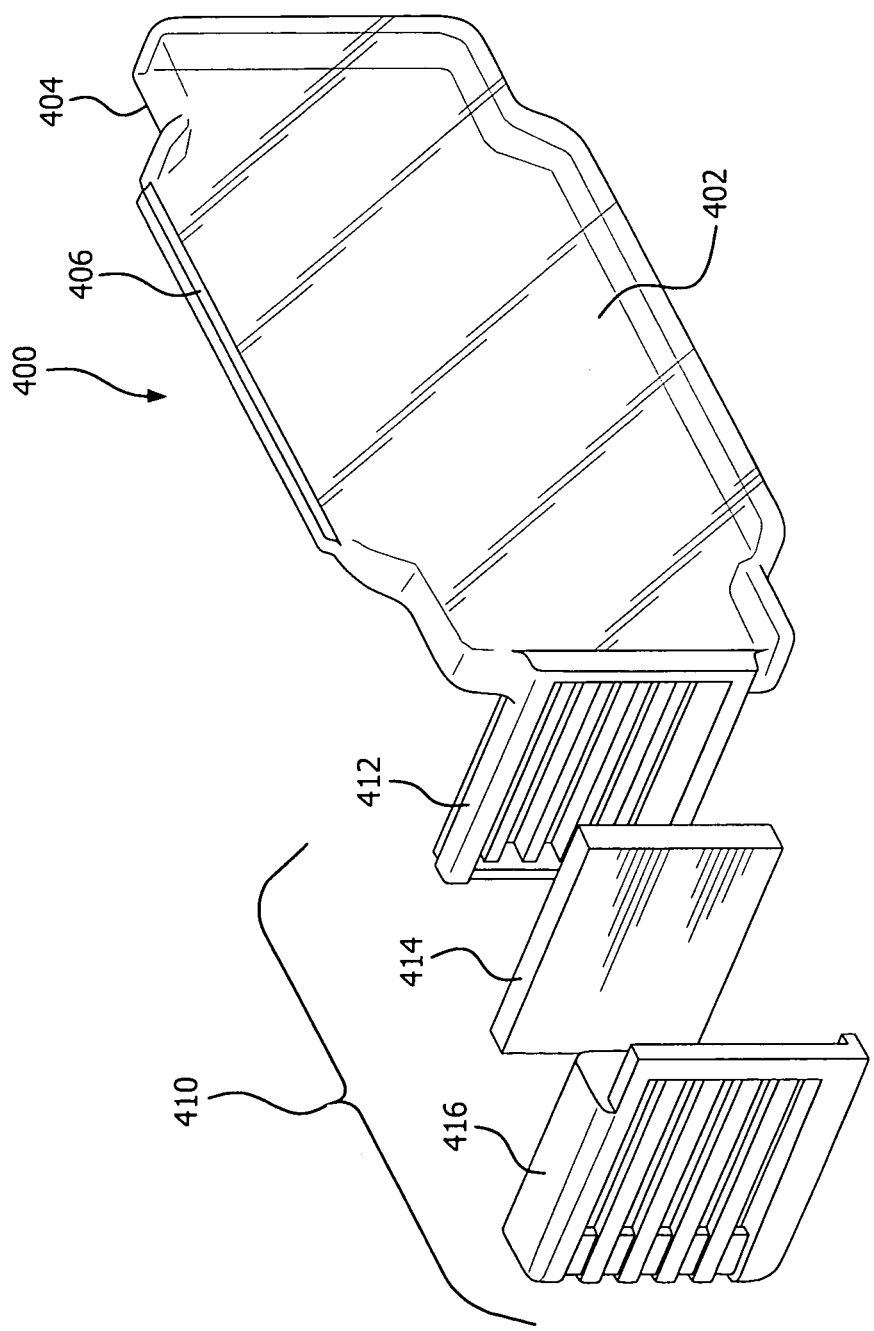
FIG. 6 is an exploded perspective view showing a splash shield and vent filter for use with an inspection lamp.

As shown in FIG. 6, another embodiment of a removeable ultraviolet-transmitting splash shield 400. The shield 400 includes a lens 402 and a rim 404 for fastening the shield 400 to the housing 12. The shield 400 can include a tab 406 to aid in retaining the shield 400 on the lamp 10. The shield 400 is preferably made from a material that is at least partially transparent to UV and visible light. In the depicted embodiment, the shield 400 includes a filter assembly 410 for filtering air on the inlet side of a fan mounted inside the lamp 10. The filter assembly 410 includes a filter back grate 412 that is integral with the shield 400 and located so as to be positioned generally in front of the inlet to the fan. A filter cover 416 is removably attached to the back grate 412. A replaceable filter element 414, such as pleated or quilted conventional filter media) is mounted between the filter back grate 412 and the filter cover 414.

Various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. An inspection lamp with interchangeable mount comprising:
   a housing having a front and rear;
   at least one LED mounted in or to the housing for emitting light in a blue or ultraviolet wavelength range from the front of the housing;
   a mounting apparatus adapted to removably mount the housing to a mounting fixture, the mounting apparatus including a lamp adapter for engaging with the lamp housing; and
   a retention device on the housing for engaging with the lamp adapter to removably retain the housing on the mounting apparatus;
   wherein the mounting apparatus further includes a fixture adapter hingedly mounted to the lamp adapter, the fixture adapter being removably mountable to the mounting fixture such that the inspection lamp can pivot upward-angled and downward-angled with respect to the mounting fixture.

2. The inspection lamp of claim 1, wherein the retention device is a slot located in the rear of the housing for slidably receiving the lamp adapter.

3. The inspection lamp of claim 2, wherein the mounting apparatus further includes a fixture adapter mounted to the lamp adapter, the fixture adapter being removably mountable to a lamp fixture in order to removably mount the housing to the lamp fixture via the mounting apparatus.

4. The inspection lamp of claim 1, wherein the lamp adapter includes a mounting tab adapted to be received into the slot in the rear of the housing.

5. The inspection lamp of claim 4, wherein the lamp adapter further includes a spring-loaded securing mechanism for preventing accidental disengagement of the slot in the rear of the housing from the mounting tab of the lamp adapter.

6. The inspection lamp of claim 1, further comprising a splash shield removably mounted to the front of the housing for protecting the LEDs, the splash shield being at least partially transparent to ultraviolet and broad spectrum visible light.

7. The inspection lamp of claim 6, the splash shield including a filter assembly for filtering air drawn into the housing.

8. The inspection lamp of claim 1, further comprising a reflector located behind each LED for directing emitted light from said LED toward the front of the housing.

9. The inspection lamp of claim 1, further comprising a lens located in front of each LED for focusing emitted light from said LED.

10. The inspection lamp of claim 1, further comprising a lens located in front of each LED for dispersing emitted light from said LED.

11. The inspection lamp of claim 1, wherein the mounting fixture comprises a head mounting fixture including straps adapted to secure the lamp to a user's head.

12. The inspection lamp of claim 1, wherein the mounting fixture comprises a spray can mounting fixture adapted to engage a portion of a spray can so as to permit light from the LEDs to emit in the direction of an item being sprayed by the spray can, the mounting fixture adapted to position the LEDs above a spray nozzle on the spray can.

13. The inspection lamp of claim 1, wherein the housing includes vents on the side of the housing for permitting air to pass between the outside and inside of the housing, and wherein a splash shield is removably mounted to the front of the housing for protecting the LEDs, the splash shield being at least partially transparent to ultraviolet and broad spectrum visible light, the splash shield including a filter assembly for filtering air drawn into the housing.

14. The inspection lamp of claim 1, wherein the light emitted by the at least one LED which emits light in a blue or ultraviolet wavelength range is in a wavelength at or below 400 nm.

15. The inspection lamp of claim 1, further comprising at least one LED mounted in or to the housing for emitting broad spectrum visible light from the front of the housing.

16. An inspection lamp with an interchangeable mount kit comprising:
 a housing having a front and rear;
 at least one LED mounted in or to the housing for emitting light in a blue or ultraviolet wavelength range from the front of the housing;
 at least one LED mounted in or to the housing for emitting broad spectrum visible light from the front of the housing;
 a plurality of mounting apparatus adapted to removably mount the housing to a mounting fixture, each mounting apparatus including a lamp adapter for engaging with the lamp housing, at least one head mounting fixture including straps adapted to secure the lamp to a user's head, and at least one spray can mounting fixture adapted to engage a portion of a spray can so as to permit light from the LEDs to emit in the direction of an item being sprayed by the spray can, the mounting fixture adapted to position the LEDs above a spray nozzle on the spray can; and
 a retention device on the housing for engaging with the lamp adapter to removably retain the housing on the mounting apparatus.

\* \* \* \* \*